(12) United States Patent
El Shami

(10) Patent No.: US 6,756,233 B1
(45) Date of Patent: Jun. 29, 2004

(54) METHOD FOR MEASURING FREE LIGANDS IN BIOLOGICAL FLUIDS, AND ASSAY KITS FOR MEASURING SAME

(76) Inventor: A. Said El Shami, 29974 Rolling Ridge Dr., Agoura Hills, CA (US) 91301

( * ) Notice: Subject to any disclaimer, the term of this patent is extended or adjusted under 35 U.S.C. 154(b) by 0 days.

(21) Appl. No.: 09/036,819

(22) Filed: Mar. 9, 1998

Related U.S. Application Data

(60) Continuation of application No. 07/303,712, filed on Jan. 27, 1989, now abandoned, which is a division of application No. 06/784,857, filed on Oct. 4, 1985, now abandoned.

(51) Int. Cl.⁷ ................ G01N 33/53; G01N 33/566; G01N 33/534; G01N 33/567; G01N 33/545
(52) U.S. Cl. ............... 436/500; 436/501; 436/504; 436/542; 436/531; 436/543; 436/545; 436/817; 436/804; 435/7.1; 435/7.93
(58) Field of Search ............... 436/500, 501, 436/504, 531, 542, 543, 545, 804, 817; 435/7.1, 7.93

(56) References Cited

U.S. PATENT DOCUMENTS 4,366,143 A * 12/1982 Midgley et al. ............. 436/501

FOREIGN PATENT DOCUMENTS

| EP | 0155104 | * | 9/1985 |
| GB | 2085160 | * | 4/1982 |

OTHER PUBLICATIONS

Felicetta et al. J. Clin. Endocrinol. Metabol. 57: 207–212, 1983.*
Amino et al. Clin. Chem. 29: 321–325, 1983.*
Tabachnick et al. Arch. Biochem. Biophys. 136: 467–479, 1970.*
Corning Product Brochure: Single Step Free T4 [125I] Radioimmunoassay, IMMO Phase, May, 1984.*
Corning Product Brochure: Single Step Free T4 [125I] Radioimmunoassay, IMM) Phase, Jan. 1983.*

* cited by examiner

*Primary Examiner*—S. Devi
(74) *Attorney, Agent, or Firm*—Joseph E. Mueth

(57) ABSTRACT

A method for measuring free ligands in biological fluids in the presence of bound ligand and endogenous binding proteins, without disturbing the equilibrium between the free ligand and the protein-bound ligand, comprised of the following steps: (a) incubating a sample of biological fluid with (i) a ligand analog tracer which, due to its chemical structure, does not bind to some of the endogenous binding proteins, (ii) a specific ligand binder and (iii) specific chemical inhibitor reagents that alone or in combination inhibit the binding of the ligand analog tracer to other endogenous binding proteins; (b) separating the ligand analog tracer bound to the specific binder from unbound tracer; and (c) comparing the bound fraction in said sample to the bound fraction of a given set of known free ligand calibrators to determine the concentration of free ligand in said biological fluid.

1 Claim, 10 Drawing Sheets

METHOD FOR MEASURING FREE LIGANDS IN BIOLOGICAL FLUIDS, AND ASSAY KITS FOR MEASURING SAME

This application is a Continuation of patent application Ser. No. 07/303,712, filed Jan. 27, 1989, now abandoned, which is a Divisional Application of patent application Ser. No. 06/784,857, filed Oct. 4, 1985, now abandoned.

BACKGROUND OF THE INVENTION

For several decades equilibrium dialysis techniques were the only available method for the measurement of free hormones in serum, and until recently were the only methods considered reliable. Equilibrium dialysis methods in this context suffer from several drawbacks including poor precision, tediousness and so on; but above all their results are highly dependent on the purity of the tracers used.

Ellis and Ekins, R. (Acta Endocr. (KbH.) Suppl. 177:106, 1973), disclosed a direct method for free hormone determinations in their paper "Direct Measurement By Radioimmunoassay of the Free Thyroid Hormone Concentration in Serium." This represented a major improvement over equilibrium dialysis methods because it allowed for the direct measurement by radioimmunoassay (RIA) of free ligand levels in serum dialysates, thus circumventing the problem of tracer purity. This method is now considered by many as the reference methodology for CO free hormone measurements. It is, however, still time consuming and operator-dependent, and it is unavailable to most small laboratories.

Indirect methods for the estimation of free hormone concentrations which were introduced shortly thereafter include the testosterone/steroid hormone binding globulin (SHBG) ratio, the thyroxine (T4)/thyroid binding globulin (TBG) ratio, the free T4 index (based on the product of triiodothyronine (T3) uptake and T4), and the free androgen index.

Ekins, R. (Free Thyroid Hormones; Proceedings of the International Symposium held in Venice, December 1978, Amsterdam: Excerpta Medica, 1979 72–92), introduced the concept of "direct dynamic methods" in which an anti-free ligand antibody is used in direct contact with the biological fluid during dialysis. This constitutes the basis for so-called "immunoextraction" methods.

One such method is taught in U.S. Pat. No. 4,046,870 in which a two-tube immunoassay method measures the rate of transfer of T4 from binding proteins to T4-specific antibody. This method suffered from several analytical and clinical shortcomings which made it virtually just another free T4 index assay.

A second method, introduced by Clinical Assays (Cambridge, Mass. 02139), was a true immunoextraction method. It used a single-tube, two-stage, sequential (back-titration) technique. In this method, a serum sample is incubated with immobilized antibody; then, following a wash step, unoccupied sites on the immobilized antibody are "back-titrated" using labeled ligand. In this approach, the serum is never in contact with the labeled ligand. Although theoretically sound, it suffers from poor sensitivity and precision, and both reactions require exact timing.

Single-step immunoextraction methods for the determination of free ligand concentrations in biological specimens were the obvious next step in the development of free ligand assay systems. These methods rely on chemical rather than physical separation of labeled ligand from nedogenous binders. In order to achieve this objective, several approaches can be adopted, as detailed below.

The prior art discloses that by chemically altering the structure of a given ligand, its binding to endogenous binders is reduced or diminished. This has been amply demonstrated for steroid hormones. (See the discussion of free testosterone below.) In the case of thyroid hormones, Ross, J. E. and Tapley, D. F. (Effect of various analogues on the binding of labeled thyroxine to thyroxine-binding globulin and prealbumin, Endocrinology 79:493, 1966), have shown that the binding of TBG (thyroid binding globulin) to T4 is inhibited if a fairly bulky substitution is made at the 3' position of the T4 molecule. In addition, Schall, R. F., et al (An enzyme-labeled immunoassay for the measurement of unsaturated thyroid hormone binding capacity in serum and plasma, Clin. Chem. 25:1078 (abstract) 1979), and Kleinhammer, G., et al (Enzyme immunoassay for determination of thyroxine binding index, Clin. Chem. 24:1033, 1978), independently demonstrated that TBG fails to bind to conjugates formed by labeling T4 with horseradish peroxidase. This fact constitutes the basis for the single-step immunoextraction method described in U.S. Pat. No. 4,410,633 to Corning Glass Works, for the measurement of free thyroxine and free 3,5,3'-triiodothyronine wherein horseradish peroxidase is chemically attached to T4 and T3 and later radiolabeled.

In addition, the prior art also discloses that T3 and T4 require the following molecular structure for maximal binding to endogenous binding proteins, viz. TBG, thyroid binding pre-albumin (TBPA), albumin, Snyder, S. M, et al (Binding of thyroid hormones and their analogues to thyroxine-globulin in human serum, J. Biol. Chem. 251:6489, 1976); Sterling, K., et al (Equilibrium dialysis studies of the binding of thyroxine by human serum albumin, J. Clin. Invest. 41:1021, 1962):

1. The L-alanine side chain configuration:
2. The presence of 4'-hydroxyl group (primarily for TBPA and albumin binding); and
3. The presence of two (halogen) substituents in the inner and outer rings (positions 3,5,3' and 5').

Several hundred T3 and T4 analogs have been synthesized and studied for their ability to bind to thyroid hormone binding proteins.

U.S. Pat. No. 4,366,143 and its European counterpart, Patent No. 00 26 103, broadly describe the use of such analogs as tracers in a single immunoextraction using simultaneous rather than sequential titration of antibody for the measurement of free hormones. (For convenience, these patents will be collectively referred to hereinafter as the "Amersham" patent.)

An intact alanine side chain is required for optimal binding of T4 and T3 to TBG: the amino group on the analine side chain is the essential constituent. Analogs described in the Amersham patent are T3 and T4 molecules modified at the alanine side chain. Although theoretically these analogs do not bind TBG to any significant extent, they undoubtedly bind albumin and TBPA significantly since the 4'-hydroxyl group on the T3 and the T4 molecules is left intact. It is well established that the binding of albumin and TBPA to the thyronines is quantitative, especially under physiological conditions, Sterling, K. (Molecular structure of thyroxine in relation to its binding by human serum albumin, J.Clin Invest. 43:1721, 1964), and Pages, et al (Binding of thyroxine and thyroxine analogs to human serum prealbumin, Biochem 12:2773, 1973).

The failure of the Amersham patent to recognize the importance of albumin and TBPA binding to the thyronines renders the patent's teachings inadequate for the true measurement of free T3 and free T4 in biological fluids. In fact the commercially available reagents eased on the patent yield misleading and inaccurate free hormone results. This is particularly true in several pathological conditions characterized by significant alterations in the circulating albumin level.

Recent literature has shown that the albumin concentration correlates directly with free T4 concentrations generated by the Amersham assay system. In addition, it is well documented that Amersham's method consistently yields falsely decreased free T4 results in third-trimester pregnancies and in patients suffering from severe non-thyroidal illness, while yielding falsely elevated free T4 levels in cases of familial dysalbuminemic hyperthyroxinemia, a condition in which T4 is abnormally bound to circulating albumin.

During pregnancy, albumin circulates at lower than normal levels, especially during the third trimester. Since Amersham's labeled analog T4 tracer binds albumin and TBPA to a significant extent (greater than 99%), one would expect the Amersham assay system to yield lower than normal free T4 results during the third trimester: more analog tracer is available to bind T4 antibody, resulting in higher binding and lower apparent dose.

Non-esterified free fatty acids are capable of displacing labeled analog from albumin; moreover, they circulate at higher than normal concentrations during pregnancy. This could explain the lower than expected free T4 values encountered during pregnancy when assayed by the Amersham method; apparent free T4 levels would be significantly lower than expected if albumin binding to the labeled analog is substantial.

This Situation is also well documented in cases of heparin therapy, where a significant elevation of non-esterified free fatty acids is present. Free T4 and free T3 levels when measured by Amersham's method on heparin-treated patients show lower than normal levels.

The same problem occurs for non-thyroidal illness, where free T3 and T4 values generated by the Amersham method have been shown to be significantly lower than for a euthyroid population, when compared to a direct equilibrium dialysis method.

The Amersham patent procedure has been found wanting by workers in the art as manifested by the observance of false and erroneous measurements of free ligand levels. Applicant has discovered that the problem stems from binding of the ligand analog tracer to certain endogenous proteins, e.g., albumin in biological fluids. I have discovered that this problem can be overcome by the use of specific chemical inhibitor reagents. This discovery represents a major advance in the art and it is believed to be deserving of a patent.

SUMMARY OF THE INVENTION

Briefly, this invention comprises a method for measuring free ligands in biological fluids in the presence of bound ligand and endogenous binding proteins, without disturbing the equilibrium between the free ligand and the protein-bound ligand, comprised of the following steps: (a) incubating a sample of biological fluid with (i) a ligand analog tracer which, due to its chemical structure, does not bind to some of the endogenous binding proteins, (ii) a specific ligand binder and (iii) at least one specific chemical inhibitor reagent that inhibits the binding of the ligand analog tracer to other endogenous binding proteins; (b) separating the ligand analog tracer bound to the specific binder from unbound tracer; and (c) determining the concentration of free ligand in said biological fluid.

It is an object of this invention to provide a new and improved method for measuring free ligands in biological fluids.

More particularly, the present invention has as its object the truer measurement of free ligands in biological fluids.

These and other objects and advantages of my invention will be apparent from the detailed description which follows.

DETAILED DESCRIPTION OF THE PRESENT INVENTION

The present invention addresses the deficiencies encountered in the Amersham patent and effectively corrects for the inconsistencies in free thyroid results generated by Amersham's analog method.

The present invention uses labeled analogs for T3 and T4 that are modified at the analine side chain. Specifically, the α-amino group is modified to prevent their binding to TBG. Meanwhile, steps have been taken to prevent such labeled analogs from binding to albumin and TBPA. This is accomplished by carefully selecting an exogenous chemical reagent or reagents that alone or in combination are able to bind to unoccupied binding sites on the albumin and TBPA molecules, thus saturating these binding proteins and effectively eliminating their capacity to bind to thyronine analogs and to other endogenous substances such as non-esterified free fatty acids. These exogenous chemicals should not bind to TBG and their concentration should be such as not to displace any bound hormone from albumin or TBPA.

The association constant for albumin and T4 is approximately 500,000. (This estimate is based on the assumption that the number of binding sites on the albumin molecule available for thyroxine is equal to 1, and that the apparent association constant in liters per mole—i.e. the equilibrium constant in the direction of complex formation—is $5 \times 10^5$.) Likewise, the association constant for albumin and T3 is approximately 24,600. It is well established that albumin has a higher affinity for free T3 and T4 and their analogs than for anionic dyes, but a much higher affinity for free fatty acids than T3 and T4 and their analogs.

Albumin has a relatively low association constant for single aromatic compounds; the highest association constants are for 2,4-dinitrophenol (11,000) and salicylate (2,800).

In order to maintain strict equilibrium conditions in vitro during the immunoextraction reaction one has to maintain strict physiological conditions; this entails the use of pH=7.4. At that pH, thyronine molecules have three charged groups: the anionic carboxylate ion, the cationic α-amino group and the anionic phenolate ion. (The latter is 82% ionized.) The presence of albumin or TBPA under these physiological conditions yields a highly charged albumin with a relatively large number of catiohic amino groups. These cationic amino groups on the albumin molecule bind the anionic phenolate ion on the thyronine molecules. Such an interaction is the main cause of albumin binding to the labeled analog in both the Amersham patent method and the Corning patent method.

The present invention makes use of the fact that 2,4-dinitrophenol (DNP) and sodium salicylate with their relatively high association constants to albumin and TBPA will also be ionized and charged under these physiological conditions of pH, yielding charged anionic phenolate ion capable of interaction with the charges on the albumin and TBPA molecules. When either 2,4-dinitrophenol or sodium salicylate or both are present in excess, the binding of labeled T3 and T4 analogs to albumin and TBPA is virtually eliminated. This method of blocking albumin and TBPA by appropriate concentrations of 2,4-dinitrophenol and/or sodium salicylate is an effective means for eliminating the erroneous assay results caused by albumin in free thyroid hormone immunoex-traction analog methods.

The present invention is applicable to a variety of other chemical inhibitor reagents, that is, reagents capable of blocking unwanted reaction of the ligand analog tracer to circulating endogenous binding proteins. The substituted monoaryl organic compounds are exemplary. The substituents on such compounds include nitro, carboxyl, carboxyl salts and the like. The monoaryl compounds have a phenolic hydroxyl group which are particularly useful. Another suitable category are the dyes such as sulfobromophthalein, orange red, bromocresyl blue and the like. The higher (over about 5 carbon atoms) fatty acids such as oleic acid are also useful. Still other compounds will be apparent to those skilled in the art. For example, many amino acids have a high affinity to albumin to and hence are useful in the practice of this invention, e.g., tryptophan. Another suitable category are T3, T4 or testosterone analogs which displace labeled analog from endogenous proteins while not binding to the antibody or other specific ligand binder.

This invention can be used to detect the concentration of any of the free ligands normally found in human body fluid. For example, the free ligand can be thyroxine, triiodothyroxine, testosterone, cortisol, progesterone, oestradiol, hormones and steroids generally, also drugs and products of drug metabolism, vitamins such as B12, toxins, and the like.

In general, specific ligand binder is one which couples or binds to the free ligand and it may be a specific antibody for the free ligand or other binding agent. In general, the specific ligand binders appropriate to the various free ligands are known and need not be further described.

The ligand analog tracer is labeled in some way so as to be detectable or observable. Radiolabels are well-known and applicable, as are the other labeling means previously employed in this art, including enzymes, fluorophors, chromophores and chemiluminescent groups integral with the ligand analog tracer molecule.

FREE THYROID HORMONES

Figure 1:
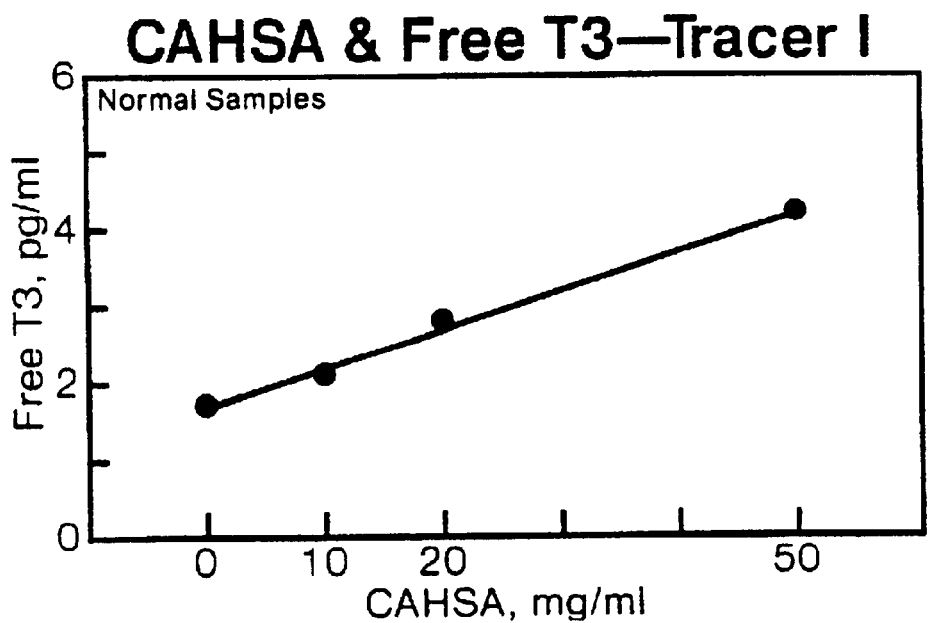
FIGS. 1 to 4 demonstrate that charcoal-absorbed human serum albumin (CAHSA) has no effect on free T3 when sera from normal individuals and tracer I, II, III and IV respectively were used.

Antibodies to both L-thyroxine and 3,5,3'-triiodothyronine were produced in rabbits by well-established, conventional techniques using bovine serum albumin-T4 and -T3 as the immunogens.

Analogs of diiodothyronine (T2) and T3 were prepared by sucinylating the $\alpha$-amino group on the analine side chain to produce N-L-diiodothyronine succinamide and N-L-triiodothyronine, respectively, which were then iodinated by conventional iodination procedures to produce, respectively, N-$^{125}$I-L-triiodothyronine succinimide and N-$^{125}$I-L-thyroxine succinamide. The tracers were then compounded in 0.01 M HEPES (N-2-hydroxyethylpiperazine-N'-2-ethanesulfonic acid) buffer, pH 7.4 and 0.01% sodium aside. 0.1 M charcoal-absorbed human serum albumin (CAHSA) free of any apparent T3 or T4, and blocking agents were added as described in specific examples below. Different amounts of T3 or T4 were added to human serum free of any apparent T3 and/or T4, calibrated in terms of direct equilibrium dialysis, and assigned values for each level.

T3 and T4 antibodies were immobilized on the inner walls of polypropylene 12×75 mm tubes by passive adsorption as described in Catt, K., et al (Solid phase radioimmuoassay in antibody-coated tubes, Science 158:1570, 1967).

For the assay of free T4, 50 $\mu$l of calibrator or patient sample is pipetted into anti-T4 antibody-coated tubes, followed by 1.0 ml of the labeled T4 analog. The tubes are then incubated for 60 minutes at 37° C. After this incubation the tubes are decanted and the bound radioactivity is counted. Results are calculated from the calibration curve and expressed in ng/dl.

For free T3 assay, 100 $\mu$l of calibrator or patient sample is pipetted into anti-T3 antibody-coated tubes, followed by 1.0 ml of labeled T3 analog tracer. The tubes are incubated for three hours at 37° C., then decanted and radioactivity counted. The results are calculated as for free T4 and expressed in pg/ml.

FREE THYROID HORMONE EXAMPLES

Example 1

The choice of antibodies for the free T3 and free T4 assay systems was determined by the fact that the free hormone is in physiological equilibrium with its transport proteins. This equilibrium should be maintained when an antibody directed against the hormone is added to the system. It is essential to select an antibody which is appropriate in terms of its affinity constant and its specificity for the free analyte. Such antibodies should also have slow reaction kinetics.

For free thyroxine (T4) an antibody with a working titer or dilution of 1:250,000 was selected (2.0 ng IgG/tube). In order to check the effect of tracer binding to the antibody in the presence and absence of albumin and albumin-blocking agents, antibody-coated tubes were prepared using titers of 1:250,000 (2.0 ng IgG/tube) and 1:25,000 (20.0 ng IgG/tube). Maximum bindings were determined following the free T4 protocol described above. The results are tabulated below in table 1.

TABLE 1

Free T4.

| | % B/T | | |
|---|---|---|---|
| Ab Titer: | 1:25.000 | 1.250.000 | |
| Tracer A | 60.8% | 63.3% | without CAHSA; no zero calibrator (system devoid of albumin) |
| Tracer B | 18.1% | 2.6% | without CAHSA; 1.0 mg albumin/tube contributed from zero calibrator (50 $\mu$l) |

TABLE 1-continued

Free T4.

| | % B/T | | |
|---|---|---|---|
| Ab Titer: | 1:25.000 | 1.250.000 | |
| Tracer C | 15.0% | 1.4% | with 1 mg CAHSA/tube; no zero calibrator |
| Tracer D | 9.4% | 0.7% | with 1 mg CAHSA/tube + 50 µl zero calibrator |
| Tracer E | 39.1% | 23.2% | with 1 mg CAHSA/tube + 50 µl zero calibrator + 0.5 mg/ml Na salicylate |
| Tracer F | 53.5% | 49.2% | with 1 mg CAHSA/tube + 50 µl zero calibrator + 5.0 mg (ml Na salicylate |
| Tracer G | 51.2% | 39.5% | with 1 mg CAHSA/tube + 50 µl zero calibrator + 1 mg (ml Na salicylate + 1 mg/ml 2,4-dinitrophenol |
| Tracer H | 58.2% | 38.6% | with 1 mg CAHSA/tube + 50 µl zero calibrator + 25 mg/ml Na salicylate + 0.15 mg/ml 2,4-dinitrophenol |

In the absence of albumin or any other protein, the binding of the analog $^{125}$I-T4 tracer to antibody at both antibody titers is of equal magnitude. In the presence of albumin-2 mg albumin/tube, contributed jointly by the tracer and the zero calibrator-the analog tracer does not bind to the higher titer antibody, while binding to the lower-titer antibody at only 9.4% (tracer D). In the presence of only 1 mg albumin/tube, the binding of tracers B and C to the high titer antibody is negligible—2.6% and 1.4%, respectively—whereas binding to the lower titer antibody is significant—18.1% and 15.0%, respectively.

The following conclusions can be drawn from the results of these experiments:
1. Albumin at concentrations of 1 to 2 mg/tube substantially binds to the tracer analog in the presence of 2.0 ng IgG antibody/tube.
2. 2.0 ng IgG antibody/tube has a lower affinity than albumin for the analog tracer.
3. In the presence of albumin blocking agents, the binding of labeled T4 analog to the antibody is restored.

The same experiments were also conducted for the free T3 assays. The tabulated results support similar conclusions (Table 2).

Thus, the concentration of the antibody used in a free hormone assay is critical, and must be carefully adjusted so as not to displace bound analyte from endogenous proteins. The teachings of the Amersham and Corning patents do not disclose the concentrations of the antibodies used to measure free T3 and free T4. However, based on the experiments summarized above, it can be assumed that both the Amersham and the Corning patents must have used substantially higher antibody concentrations in order to bring about reasonable binding between the antibody and the analog tracer, since neither patent employs blocking agents.

Example 2

The working antibody concentrations established on the basis of Example 1 above are 5.5 and 2.0 ng IgG/tube of T3 antibody and T4 antibody, respectively. In order to determine the appropriate albumin blocking agent or agents for use in the free T3 and free T4 assay systems, the following compounds were added to the analog tracers in the concentrations specified. (Each tracer also contained 1 mg/ml of charcoal absorbed human serum albumin.) Maximum binding was determined for each tracer. The zero calibrator was also added to each set of maximum binding tubes.

It must be emphasized that the scope of this invention is not limited to the examples used in Tables 3 through 11. They are presented here to show that, at the antibody

TABLE 2

Free T3.

| | % B/T | | |
|---|---|---|---|
| Ab Titer: | 1:9.000 | 1.90.000 | |
| Tracer A | 70.6% | 46.3% | without CAHSA; no zero calibrator (system devoid of albumin) |
| Tracer B | 6.0% | 1.0% | without CAHSA; with zero calibrator (100 µl) |
| Tracer C | 6.3% | 1.2% | with 1.0 mg/ml CAHSA/tube; no zero calibrator |
| Tracer D | 5.4% | 0.9% | witb 1.0 mg/ml CAHSA/tube + 100 µl zero calibrator |
| Tracer E | 42.9% | 22.5% | with 1.0 mg/ml CAHSA/tube + 100 µl zero calibrator + 1.0 mg/ml Na salicylate |
| Tracer F | 59.2% | 35.0% | with 1.0 mg/ml CAHSA/tube + 100 µl zero calibrator + 5 mg/ml Na salicylate |
| Tracer G | 46.0% | 23.1% | with 1.0 mg/ml CAHSA/tube + 100 µl zero calibrator + 1.0 mg/ml Na salicylate + 1.0 mg/ml 2,4-dinitrophenol |
| Tracer H | 57.7% | 28.5% | with 1.0 mg/ml CAHSA/tube + 100 µl zero calibrator + 25 mg/ml Na salicylate + 0.15 mg/ml 2,4-dinitrophenol | concentrations selected, binding of the analog tracers will increase with increasing amounts of albumin blocking reagents added, until it reaches a plateau. This also shows that binding of the T3 and T4 labeled analog is eliminated by the use of an appropriate concentration of specific albumin blocking agents.

TABLE 3

| Free T3. | |
|---|---|
| 2,4-dinitrophenol | % B/T |
| 10 µg/ml | 1.0% |
| 50 | 1.4% |
| 100 | 2.6% |
| 150 | 4.3% |
| 200 | 5.3% |
| 400 | 10.0% |
| 800 | 16.3% |
| 1000 | 17.2% |
| 3000 | 28.2% |
| 3500 | 27.6 |
| 4000 | 27.3% |

TABLE 4

| Free T3. | |
|---|---|
| oleic acid | % B/T |
| 0.0125 mmol/l | 1.2% |
| 0.025 | 1.3% |
| 0.05 | 1.3% |
| 0.125 | 1.7% |
| 0.25 | 3.5% |
| 0.375 | 12.5% |
| 0.50 | 17.6% |
| 0.75 | 16.0% |
| 1.0 | 15.5% |

TABLE 5

| Free T3. | |
|---|---|
| sodium salicylate | % B/T |
| 0.25 mg/ml | 8.8% |
| 0.50 | 14.0% |
| 1.0 | 21.3% |
| 2.0 | 26.7% |
| 5.0 | 35.8% |
| 10.0 | 36.7% |
| 20.0 | 33.3% |
| 25.0 | 30.4% |
| 30.0 | 27.8% |

TABLE 6

| Free T3. | | |
|---|---|---|
| sodium salicylate | 2,4-dinitrophenol | % B/T |
| 1.0 mg/ml | 1.0 mg/ml | 20.3% |
| 5.0 | 1.0 | 29.8% |
| 5.0 | 8.0 | 31.6% |
| 6.0 | 4.0 | 34.2% |
| 5.0 | 0.15 | 33.2% |
| 10.0 | 0.15 | 35.0% |
| 25.0 | 0.15 | 26.8% |

TABLE 7

| Free T4. | |
|---|---|
| 2,4-dinitrophenol | % B/T |
| 10 µg/ml | 2.4% |
| 50 | 4.5% |
| 100 | 8.0% |
| 150 | 11.0% |
| 200 | 13.3% |
| 400 | 22.9% |
| 800 | 31.8% |
| 1000 | 34.1% |
| 1500 | 41.4% |
| 2000 | 43.2% |
| 2500 | 43.5% |

TABLE 8

| Free T4. | |
|---|---|
| oleic acid | % B/T |
| 0.00625 mmol/l | 1.7% |
| 0.0125 | 1.7% |
| 0.025 | 1.9% |
| 0.0625 | 2.3% |
| 0.0125 | 3.5% |
| 0.1875 | 6.8% |
| 0.25 | 14.3% |
| 0.375 | 30.5% |
| 0.50 | 32.7% |
| 0.75 | 32.9% |
| 1.00 | 31.0% |

TABLE 9

| Free T4. | |
|---|---|
| sodium salicylate | % B/T |
| 0.05 mg/ml | 5.3% |
| 0.075 | 7.2% |
| 0.10 | 8.5% |
| 0.15 | 11.7% |
| 0.25 | 15.6% |
| 0.50 | 22.0% |
| 1.0 | 28.3% |
| 2.0 | 37.3% |
| 5.0 | 46.0% |
| 10.0 | 45.4% |
| 20.0 | 45.0% |
| 25.0 | 40.0% |
| 30.0 | 40.0% |

TABLE 10

| Free T4. | | |
|---|---|---|
| sodium salicylate | 2,4-dinitrophenol | % B/T |
| 1.0 mg/ml | 1.0 mg/ml | 44.1% |
| 5.0 | 1.0 | 49.8% |
| 5.0 | 0.8 | 48.1% |
| 5.0 | 0.4 | 48.2% |
| 5.0 | 0.15 | 46.4% |
| 10.0 | 0.15 | 48.8% |
| 25.0 | 0.15 | 42.6% |

Example 3

The following experiment was designed to demonstrate that albumin has no effect on the free T3 and free T4 assay systems.

Figure 2:
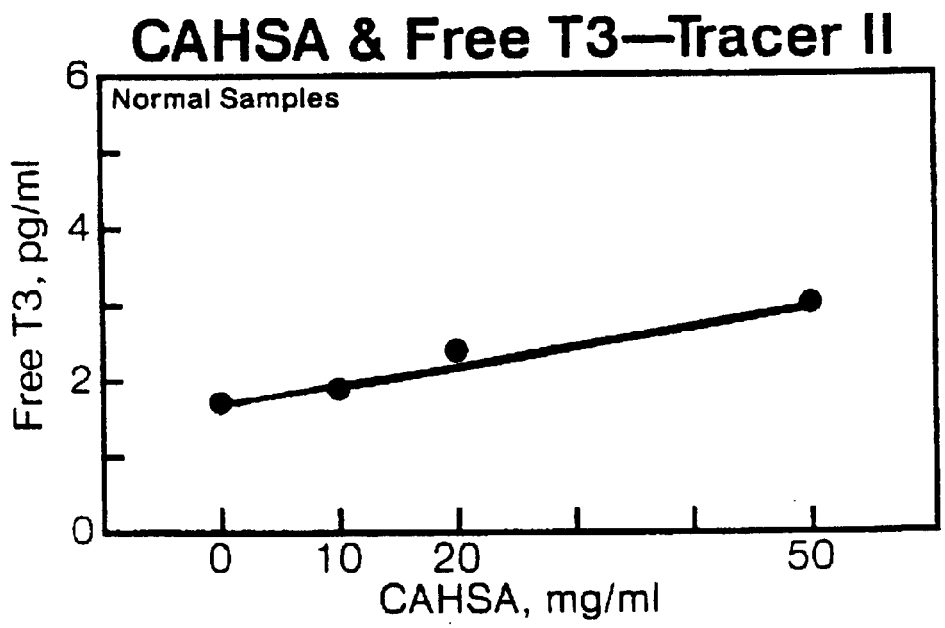
Figure 3:
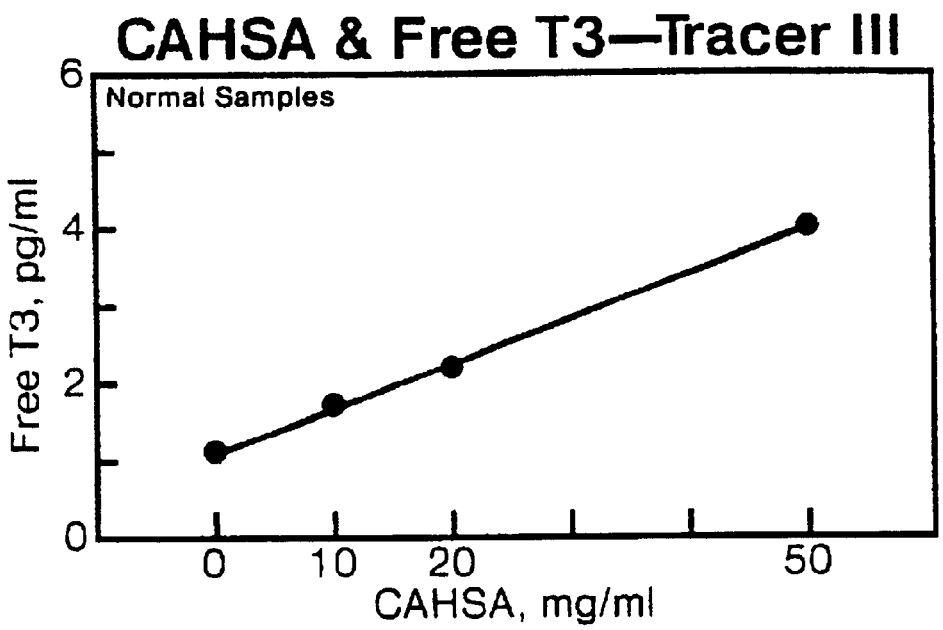
Figure 4:
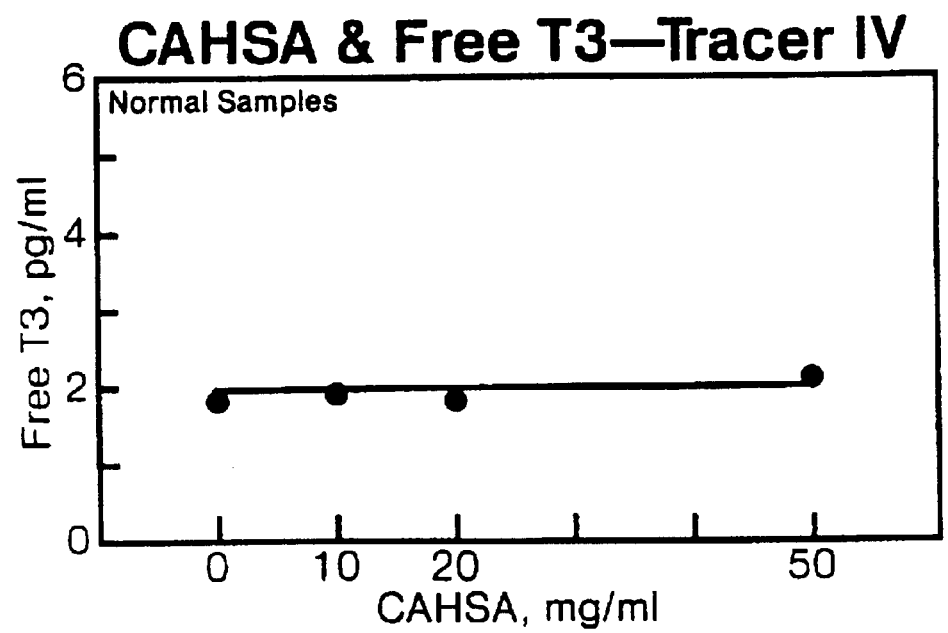
Figure 5:
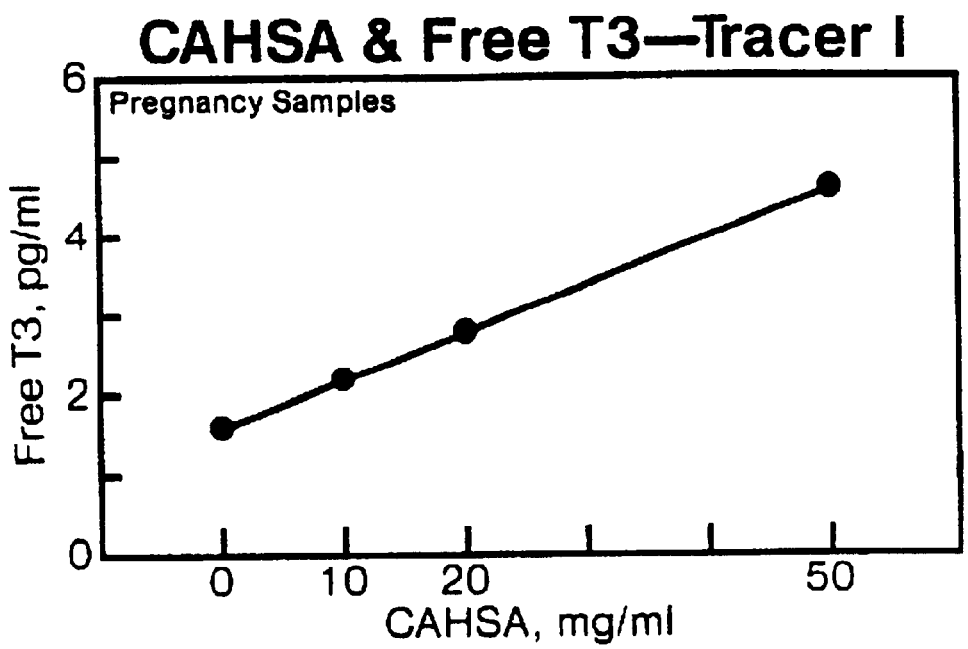
FIGS. 5–8 demonstrate that CAHSA has no effect on free T3 when pregnancy samples and tracer I, II, III and IV respectively were used.
Figure 6:
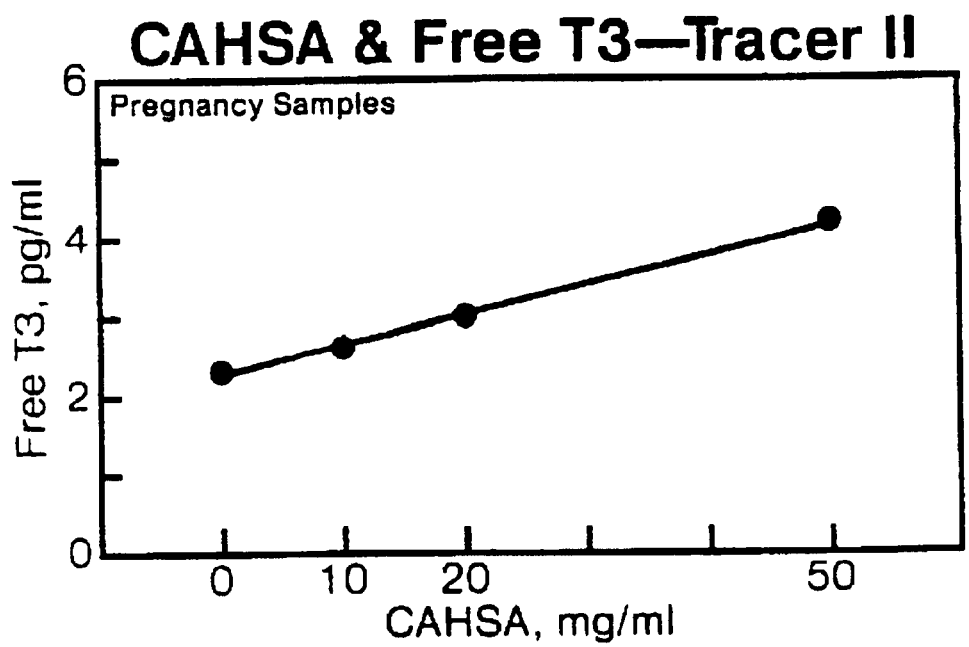
Figure 7:
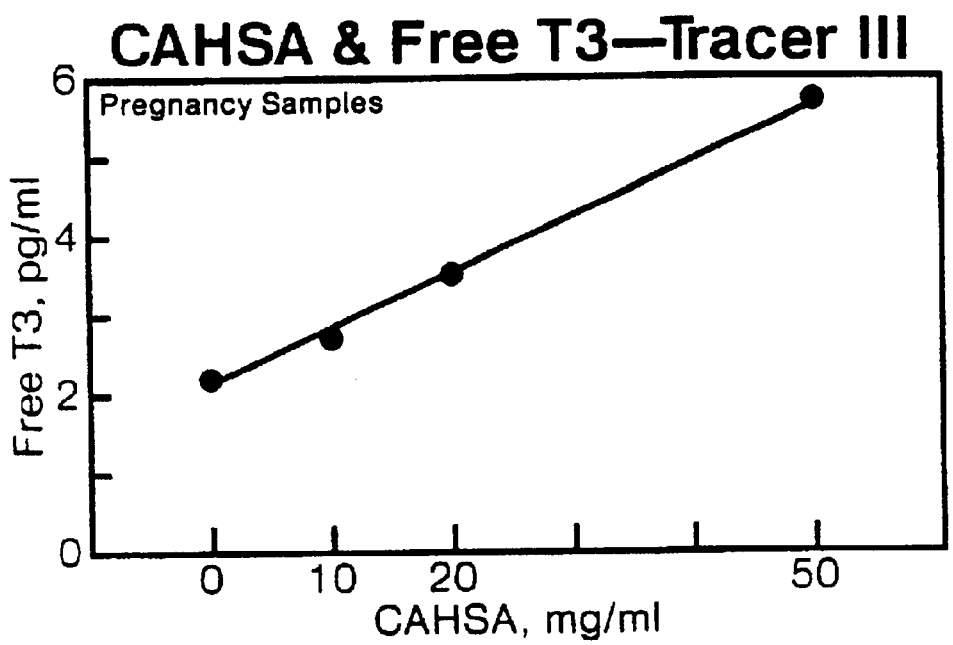
Figure 8:
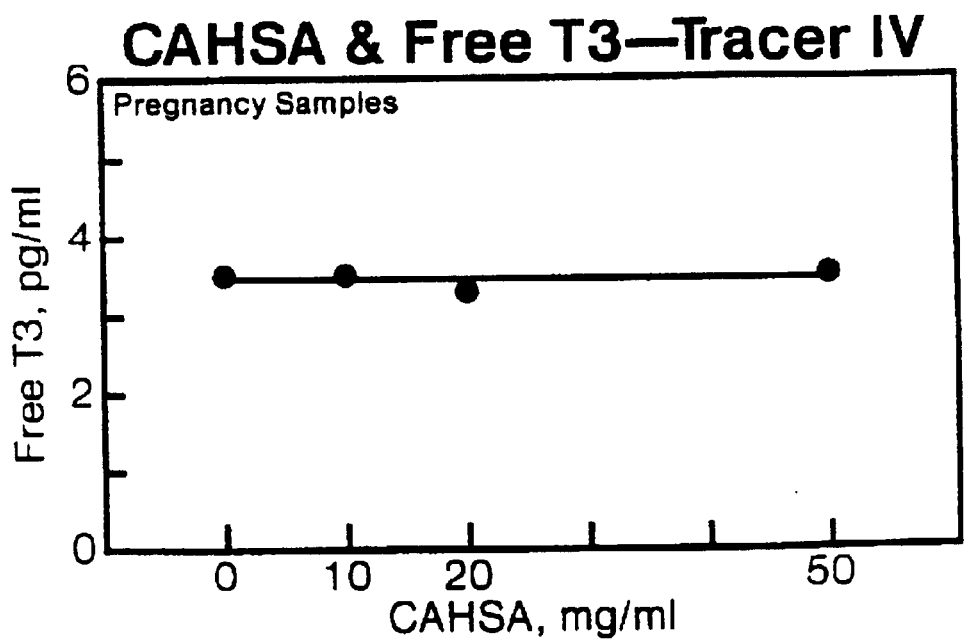
Figure 9:
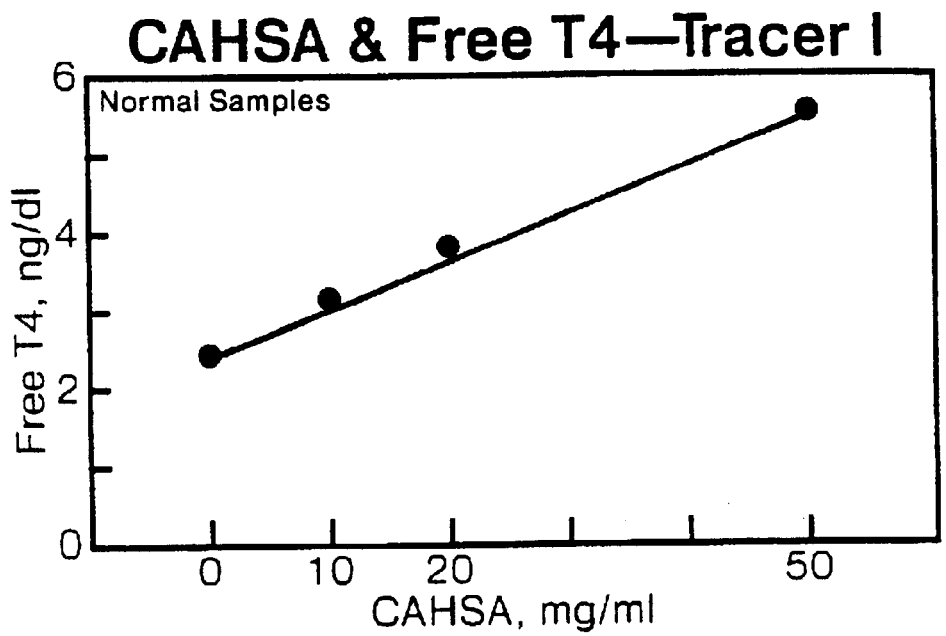
FIGS. 9–12 demonstrate that CAHSA has no effect on free T4 when sera from normal individuals and tracer I, II, III and IV respectively were used.
Figure 10:
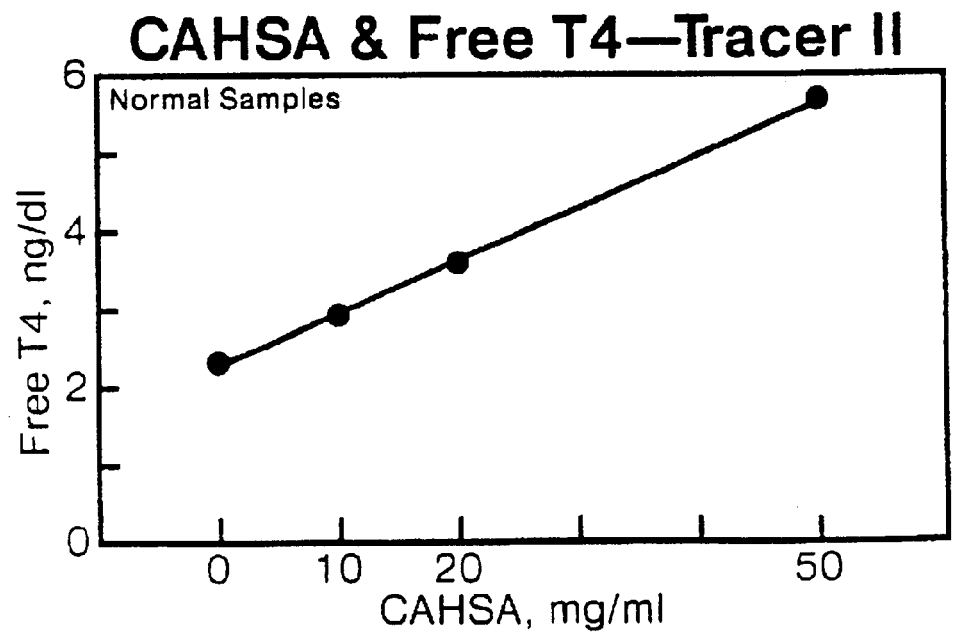
Figure 11:
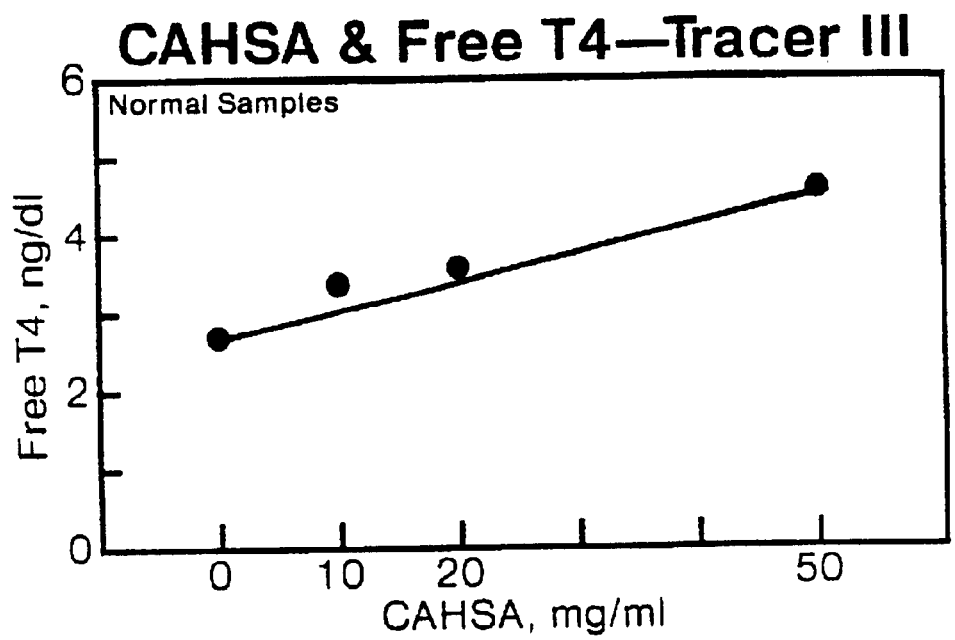
Figure 12:
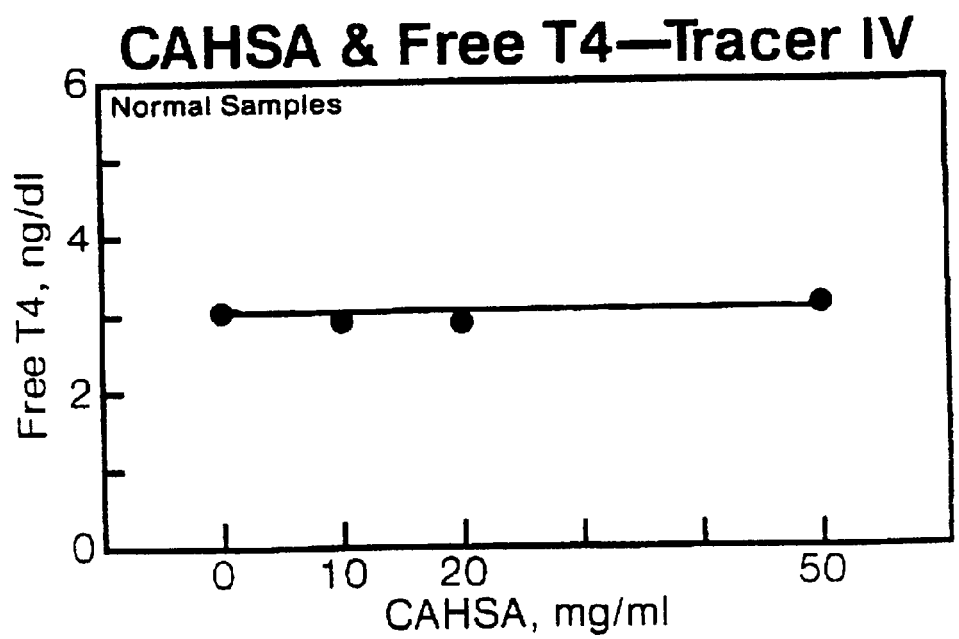
Figure 13:
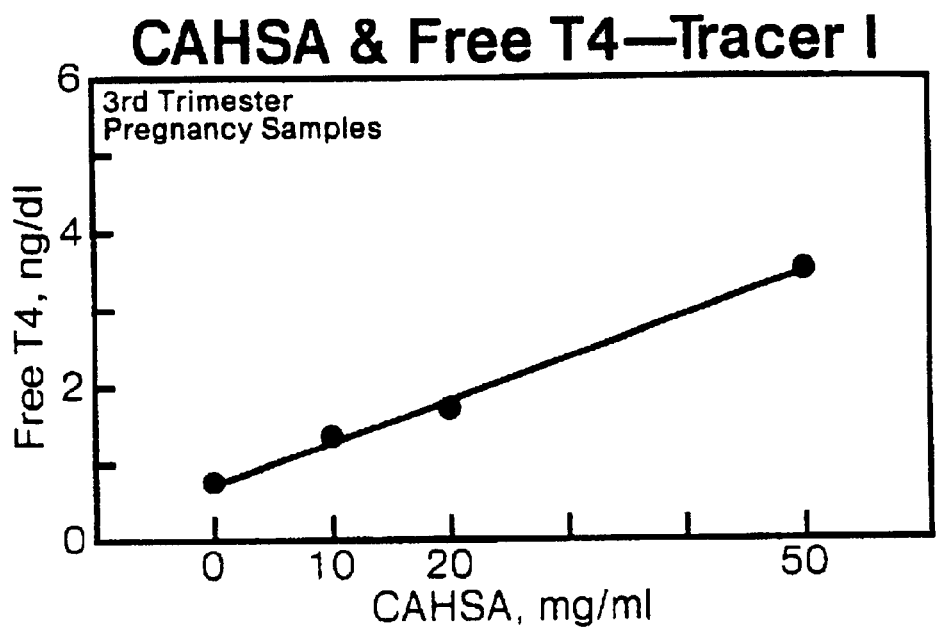
FIGS. 13–16 demonstrate that CAHSA has no effect on the free T4 when third trimester pregnancy serum samples and tracer I, II, III and IV respectively were used.
Figure 14:
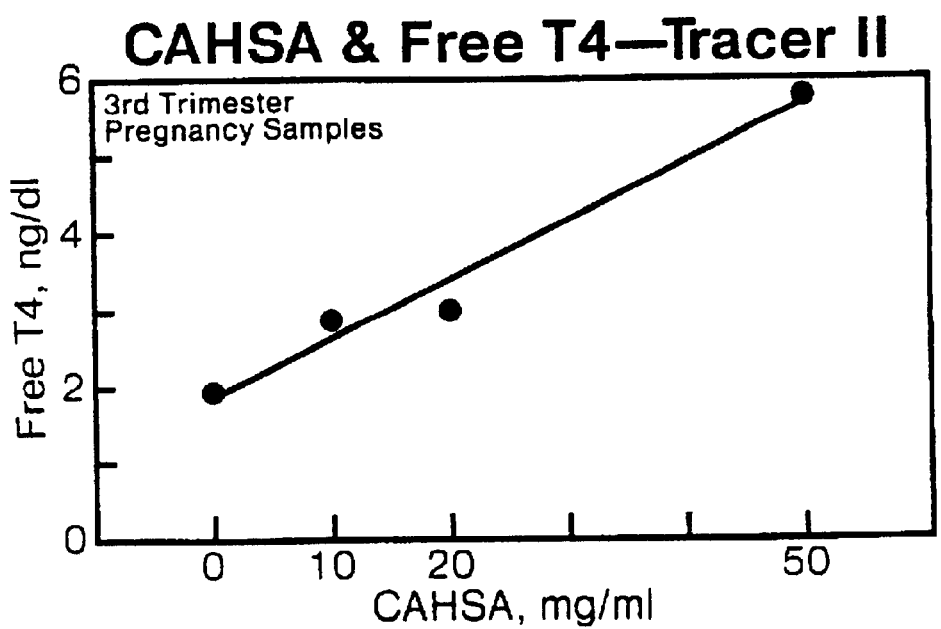
Figure 15:
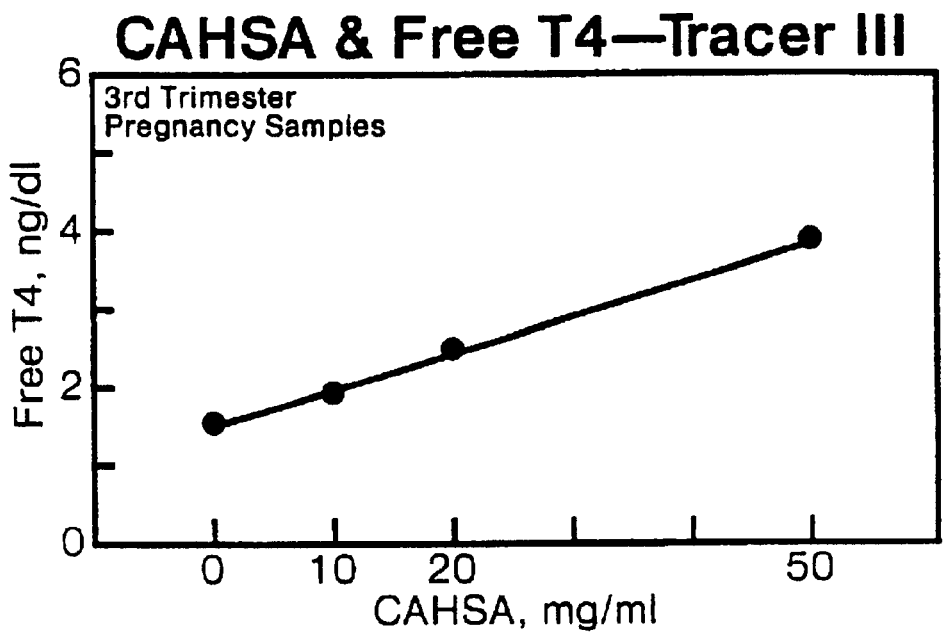
Figure 16:
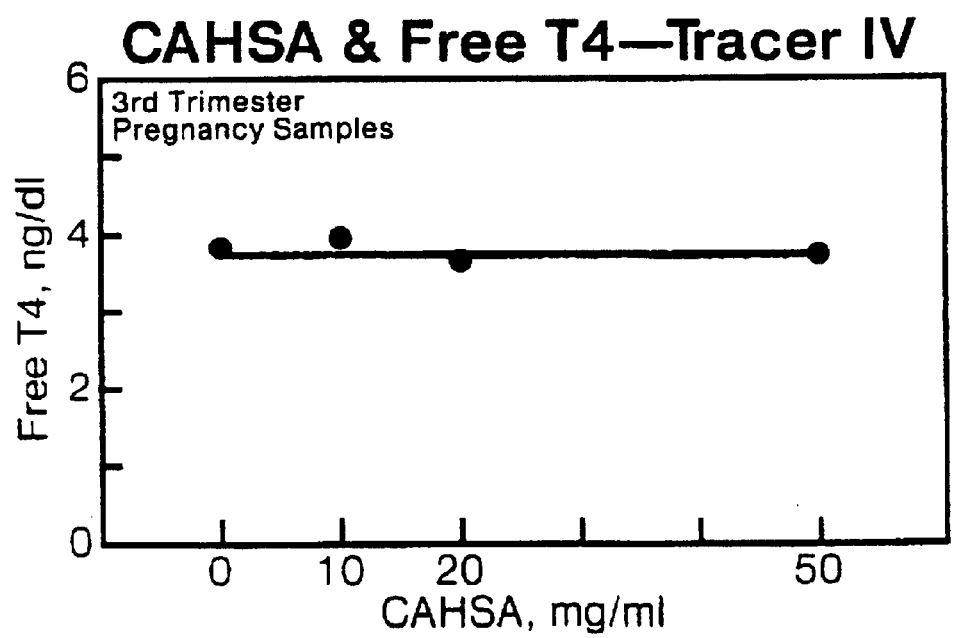

Ten samples—5 from normal individuals and 5 from females in the third trimester of pregnancy—were each divided into 4 aliquots. To three of these aliquots, lyophilized charcoal-absorbed human serum albumin was added in concentrations of 10, 20 and 50 mg/ml. The four aliquots were then processed in duplicate, as described above, in free T3 and free T4 assays using four different tracers. The mean value for each albumin concentration (N=5) was then plotted for each tracer (FIGS. 1 to 16). For free T3 and free T4, the tracers are as follows:

TABLE 11

Free T4 Tracers.

| | |
|---|---|
| Tracer I | contains 0.5 mg/ml sodium salicylate |
| Tracer II | contains 1 mg/ml sodium salicylate and 1 mg/ml 2,4-dinitrophenol |
| Tracer III | contains 5 mg/ml sodium salicylate |
| Tracer IV | contains 25 mg/ml sodium salicylate and 0.15 mg/ml 2,4-dinitrophenol |

TABLE 12

Free T3 Tracers.

| | |
|---|---|
| Tracer I | contains 1 mg/ml sodium salicylate |
| Tracer II | contains 1 mg/ml sodium salicylate and 1 mg/ml 2,4-dinitrophenol |
| Tracer III | contains 5 mg/ml sodium salicylate |
| Tracer IV | contains 25 mg/ml sodium salicylate and 0.15 mg/ml 2,4-dinitrophenol |

It is evident from the outcomes of these experiments that results generated by tracer IV for both free T3 and free T4 are unaffected by the addition of albumin up to 5.0 gm/dl, for an approximate total albumin concentration of 8.0 gm/dl.

Example 4

In order to determine whether thyroid binding globulin (TBG) will bind the labeled free T3 and free T4 analog tracers, the following experiment was conducted using tracer IV from Example 3. TBG resin stripped of all apparent T4 and T3 was added to the respective zero calibrator for each free T4 and free T3 assay in the concentrations specified below. The observed percent bound ($B/B_o$) values are shown in the Table.

TABLE 13

| | % $B/B_0$ | |
|---|---|---|
| | FT4 | FT3 |
| zero cal | 100% | 100% |
| +10 mg/ml | 95% | 99% |
| +20 mg/ml | 96% | 99% |
| +50 mg/ml | 94% | 95% |

Example 4a

This experiment was designed to check the effect of adding albumin to the zero calibrator using tracer IV from Example 3. Human serum albumin was charcoal-absorbed to remove any apparent T3 and T4 and was added to the respective zero calibrator for each free T3 and T4 in the concentrations indicated. Again, percent bound values were checked.

TABLE 14

| | % $B/B_0$ | |
|---|---|---|
| | FT4 | FT3 |
| zero cal | 100% | 100% |
| +10 mg/ml | 97% | 97% |
| +20 mg/ml | 98% | 100% |
| +50 mg/ml | 95% | 95% |

It is obvious from Examples 4 and 4a that neither albumin nor TBG binds the analog tracers under the conditions specified.

Example 5

At high concentrations, sulfobromophthalein—a dye capable of binding to albumin—is able to displace T3 and T4 from the albumin molecule. Sulfobromophthalein at low concentrations is ineffective in blocking T3 and T4 analog tracers from binding to albumin. Iodinated T4 analog was compounded as described above and divided into five aliquots. To each aliquot the following reagents were added.

TABLE 15

| | |
|---|---|
| Tracer 1 | 25 mg/ml sodium salicylate = 0.15 mg/ml 2,4-dinitrophenol (w/v) |
| Tracer 2 | 0.25 mg/ml sulfobromophthalein |
| Tracer 3 | 0.5 mg/ml sulfobromophthalein |
| Tracer 4 | 1.0 mg/ml sulfobromophthalein |
| Tracer 5 | 1.0 mmol/l oleic acid |

Each tracer was used in a separate assay for the measurement of free T4 in 20 samples under identical experimental conditions.

Considering tracer 1 as the reference and comparing the others to it, the following results were obtained.

TABLE 16

|  | Tracer 1 | Tracer 2 | Tracer 3 | Tracer 4 | Tracer 5 |
| --- | --- | --- | --- | --- | --- |
| Total CPM | 56,145 | 59,182 | 58,591 | 55,886 | 60,030 |
| % NSB | 0.5% | 0.6% | 0.6% | 0.7% | 0.5% |
| % MB | 38.6% | 18.7% | 28.6% | 27.5% | 30.4% |
| rho* | −0.9976 | −0.9964 | −0.9973 | −0.9975 | −0.9936 |
| Calibration Range ($B/B_0$) 0.1–9.0 ng/dl Intercepts ng/dl |  65.3–8.8% | 63.4–7.4% | 65.1–9.6% | 66.6–10.1% | 62.8–3.6% |
| 20% | 2.0 | 1.3 | 2.1 | 2.4 | 1.3 |
| 50% | 0.3 | 0.2 | 0.3 | 0.3 | 0.2 |
| 80% | 0.04 | 0.04 | 0.03 | 0.04 | 0.04 |
| Mean 20 samples ng dl | 1.3 | 0.6 | 1.2 | 1.7 | 0.7 |

*Correlation coefficient (an index of linearity)

TABLE 17

| Regressions | | | | |
| --- | --- | --- | --- | --- |
| Tracer 2 = | −0.42 | Tracer 1 + 1.17 | r = | −0.4914 |
| Tracer 3 = | 0.81 | Tracer 1 + 0.14 | r = | 0.945 |
| Tracer 4 = | 1.52 | Tracer 1 − 0.36 | r = | 0.956 |
| Tracer 5 = | 0.11 | Tracer 1 + 0.51 | r = | 0.268 |

The results of using tracer 3 with 0.05% sulfobromophthalein correlate significantly with those obtained using tracer 1. Results generated using tracer 3 are, however, approximately 20% lower than those generated using tracer 1. Although tracer 4 correlates well with tracer 1, it yields significantly higher free T4 values, presumably due to the release of albumin bound T4 by the high concentration (0.1%) of sulfobromophthalein.

Oleic acid added to tracer 5 is partially capable of displacing the analog tracer from albumin. However, patient data generated with this tracer show poor correlation with data generated with tracer 1, given oleic acid at this concentration. Higher concentrations of oleic acid in the tracer-concentrations greater than 1.0 mmol/l-displace bound unlabeled T4 from albumin.

Example 6

To examine the effects of nonesterified free fatty acids on the free T4 and free T3 assay systems, patient samples were aliquoted, lyophilized, and then reconstituted with different concentrations of oleic acid in distilled water. The reconstituted samples were assayed for free T3 and free T4 according to the protocol given above, using the same four tracers described in Example 3. The results, summarized in Table 18, indicate clearly that tracer 1 for free T4 is substantially bound to albumin, and that the addition of oleic acid displaces the tracer from albumin, producing spuriously low free T4 results. Tracers II and III are also bound to albumin, but to a much lesser degree. Tracer IV, however, is essentially unaffected by albumin, as shown in Example 3; moreover, oleic acid has no significant effect on free T4 values.

Results for free T3 are similar to those for free T4 in that they show tracer IV to be essentially unaffected by nonesterified free fatty acids, again confirming the results obtained in Example 3.

TABLE 18

Effect of Oleic Acid

|  | Free T4 Tracer | | | | Free T3 Tracer | | | |
| --- | --- | --- | --- | --- | --- | --- | --- | --- |
|  | I | II | III | IV | I | II | III | IV |
| Neat | 1.1 | 1.0 | 1.7 | 1.4 | 5.9 | 5.6 | 4.5 | 5.3 |
| +2.5 mmol/l | 0.4 | 0.9 | 1.1 | 1.3 | 2.4 | 3.2 | 3.7 | 5.3 |
| +5.0 | 0.3 | 0.9 | 1.1 | 1.3 | 2.7 | 2.9 | 4.2 | 5.3 |
| +7.5 | 0.3 | 0.8 | 1.1 | 1.3 | 3.2 | 2.8 | 4.2 | 5.5 |
| +10.0 | 0.4 | 0.7 | 1.2 | 1.2 | 3.6 | 3.0 | 4.4 | 5.1 |
|  | n = 3 | n = 3 | n = 4 | n = 4 | n = 3 | n = 3 | n = 4 | n = 4 |

Example 7

Figure 17:
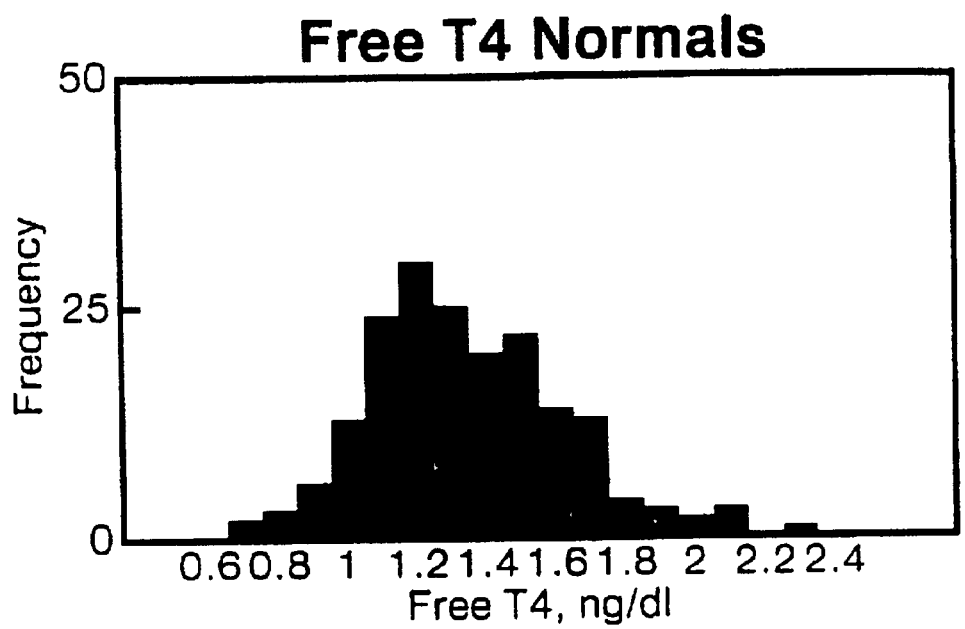
FIGS. 17–20 show the absence of statistically or clinically significant differences in free T4 values during pregnancy or non-thyroidal illness.
Figure 18:
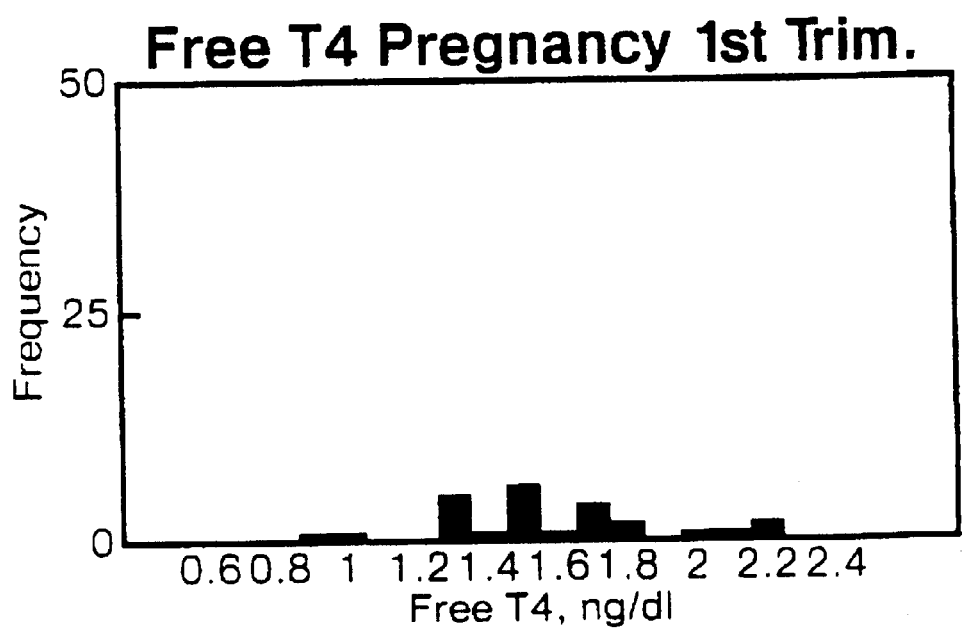
Figure 19:
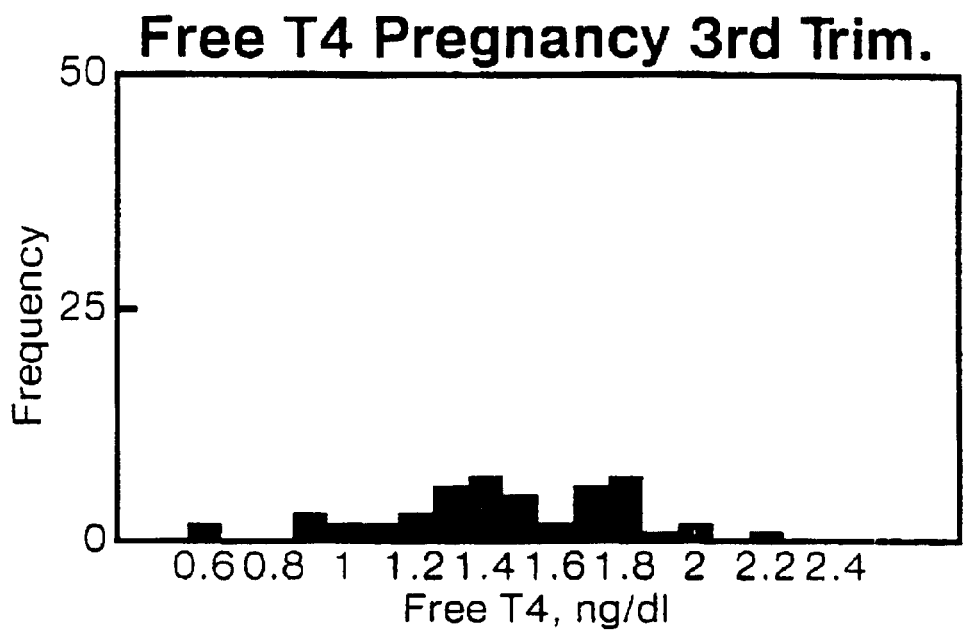
Figure 20:
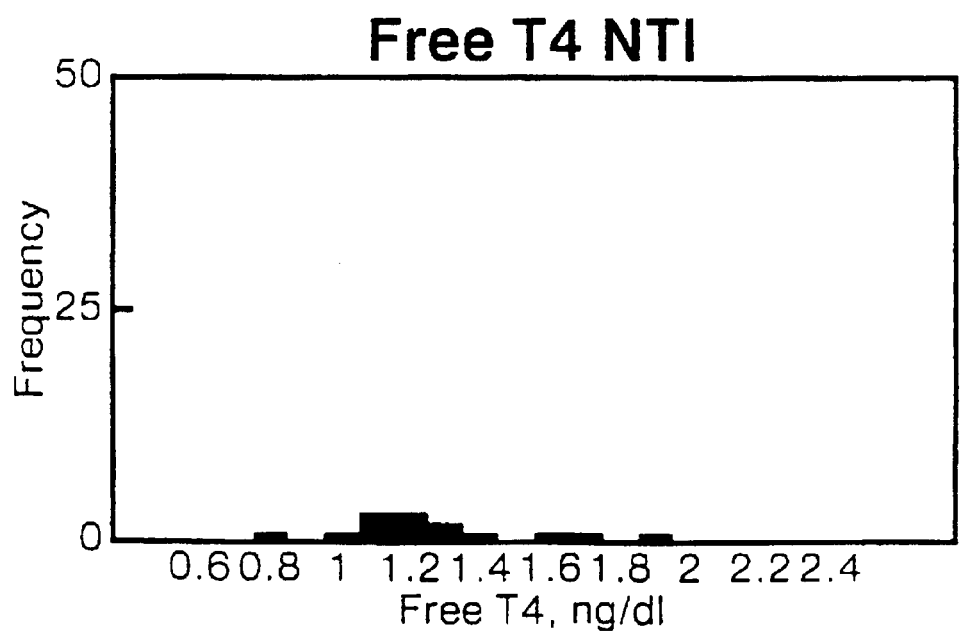

In order to establish that the results generated by the free T4 assay described above is unaffected by pregnancy and in non-thyroidal illness, 185 euthyroid samples were assayed using the tracer IV described in Example 3 above and compared to 25 first-trimester and 49 third-trimester pregnancy samples, and 14 samples from non-thyroidal illness patients. The results, summarized in Table 19 and FIGS. 17–20, show that there are no statistical or clinically significant differences in free T4 values during pregnancy or non-thyroidal illness as compared to a euthyroid population.

This again confirms the fact that when using appropriate albumin blocking reagents the free T4 assay is unaltered by *in vivo* changes in albumin concentrations.

TABLE 19

| | Free T4. | | |
| --- | --- | --- | --- |
| | 95% | Median | N |
| Euthyroids | 0.8–2.0 | 1.3 | 185 |
| Pregnancy | | | |
| 1st trimester | 0.9–2.2 | 1.5 | 25 |
| 3rd trimester | 0.7–2.1 | 1.5 | 49 |
| NTI | 0.8–1.9* | 1.2 | 14 |

*Absolute range

Free Testosterone

It is well established from prior art that steroid molecules bind to their natural binders through the A and/or B ring of the molecule. See Forest, M., et al and references therein (Free and bound steroids in plasma: methodology and physiopathological implications, In: Physiological Peptides and New Trends in Radioimmunology, C. A. Bizollon, ed., Amsterdam; Elsevier/North-Holland Biochemical Press, 1981, 249–266.) Chemical alteration of the A and/or B ring will inhibit most steroids—including testosterone, progesterone, estradiol, cortisol, and so on—from binding to endogenous binders. Testosterone was selected as a representative member of this family. A testosterone analog, 6-hydroxytestosterone-19-carboxymethyl ether histamine, was systhesized and radiolabeled with iodine 125 by conventional techniques. This analog tracer was subsequently compounded in 0.01 M HEPES buffer, pH=7.4, containing 1 mg/ml charcoal-absorbed human serum albumin and 0.01% sodium azide. Blocking agents were added, as described in the specific examples below.

Antibodies to testosterone were raised in rabbits using testosterone-19-carboxymethyl ether bovine serum albumin as the immunogen, and immobilized on the inner walls of polypropylene 12×75 mm tubes as described above for free T4 and free T3. Free testosterone calibrators, prepared by adding different amounts of testosterone to human serum free of any apparent testosterone, were calibrated by direct equilibrium dialysis and assigned free testosterone values in pg/ml. For the assay of free testosterone, 50 µl of calibrator or patient sample is pipetted into antitestosterone antibody-coated tubes, followed by the addition of 1.0 ml of iodinated 6-hydroxy-testosterone-19-carboxymethyl ether histamine analog. The tubes are incubated for 4 hours at 37° C., then decanted and radioactivity counted. Results are computed by interpolation to from the calibration curve.

FREE TESTOSTERONE EXAMPLES

Example 1

To investigate the effect of blocking agents on free testosterone results, twenty samples were assayed for free testosterone using iodinatec analog—compounded as described above—both with and without sulfobromophthalein (SBP), and with various amounts of sodium salicylate, 2,4-dinitrophenol (DNP) and 8-anilino-1-naphthalenesulfonic acid (ANS). Mean values for each tracer, in pg/ml, are summarized below.

From the example above we find that the absence of sulfobromophthalein will increase the apparent free testosterone levels by 14% since sulfobromophthalein inhibits the binding of the analog tracer to albumin without displacing testosterone bound to albumin, we also find—and this is of major importance—that salicylate, 2,4-dinitrophenol and ANS displace testosterone from albumin and/or SHBG, thus increasing the apparent free testosterone as measured by this method.

Example 2

In order to check the efficacy of the analog tracer in the free testosterone assay, iodinated 6-hydroxytest-osterone-19-carboxymethyl ether histamine (analog tracer) was compared to iodinated testosterone-19-carboxymethyl ether histamine (regular tracer) in assays for free testosterone in patient samples.

The tracers were compounded as described above with 10 µg/ml sulphobromophthalein. In order to maintain equivalent sensitivity, adjustments were made for each tracer in the amount of antibody immobilized onto the inner wall of the propylene tubes.

Twenty patient samples were assayed following the free testosterone protocol already described, using the two tracers mentioned above. The mean free testosterone values, in pg/ml, and the regression equation are displayed below.

TABLE 22

| Tracer: | 6-Hydroxytestosterone-19-histamine-$^{125}$I | Testosterone-19-histamine-$^{125}$I |
|---|---|---|
| Mean (n = 20) | 11.0 (A) <br> A = 1.48 B + 1.24 r = 0.977 | 17.3 (B) |

The results clearly indicate that the analog 6-hydroxy-testosterone-19-histamine-$^{125}$I tracer does not bind to endogenous binders, while the tracer testosterone-19-histamine-$^{125}$I does, thus yielding approximately 50% higher free testosterone values compared to the analog tracer under identical experimental conditions.

Example 3

To investigate the effect of sex hormone-binding globulin (SHBG) levels on the free testosterone assay system, a

TABLE 20

| Tracer | mg/tube: | +5 Salicylate | +10 Salicylate | +0.15 DNP | +0.3 DNP | +1.0 ANS | +2.0 ANS |
|---|---|---|---|---|---|---|---|
| without SBP | 7.9 (A) | 13.0 (B) | 14.3 (C) | 10.5 (D) | 13.4 (E) | 18.9 (F) | 17.7 (G) |
| with SBP | 7.1 (A') | 13.1 (B') | 14.4 (C') | 9.8 (D') | 13.5 (E') | 16.6 (F') | 15.0 (G') |

The regression equations between corresponding tracers are given below.

TABLE 21

| A = 1.14 | A' - 0.21 | r = 0.991 |
|---|---|---|
| B = 1.00 | B' - 0.11 | r = 0.997 |
| C = 1.02 | C' - 0.31 | r = 0.998 |
| D = 1.11 | D' - 0.30 | r = 0.996 |
| E = 1.03 | E' - 0.52 | r = 0.997 |
| F = 1.13 | F' - 0.05 | r = 0.996 |
| G = 1.19 | C' - 0.26 | r = 0.997 |
| A' = 2.76 | F' - 2.70 | r = 0.956 |
| A' = 2.34 | G' - 1.58 | r = 0.987 | charcoal-absorbed human serum pool was spiked with 400 µg SHBG/milliliter, a level which is approximately 10 times normal. The SHBG-spiked pool, when assayed by the free testosterone procedure, showed a percent bound value of 99% $B/B_o$.

Since charcoal absorption removes testosterone from the serum pool, it should have free (and total) testosterone concentrations of zero—that is, percent bound values of approximately 100% $B/B_o$—both before and after spiking. The results show, as desired, that the analog tracer, 6-hydroxy-testosterone-19-histamine-$^{125}$I, does not bind to even high levels of SHBG.

Example 4

In order to investigate the effect of elevated albumin levels on the free testosterone procedure, three lyophilized samples were reconstituted with aqueous solutions containing 0, 1.0, 2.0 and 3.0 gm/dl of charcoal-absorbed human serum albumin. All samples were assayed in parallel using the same tracer as in Example 3, with the following results.

TABLE 23

| Sample | Unspiked | Spiked with Albumin (gm/dl) | | |
|---|---|---|---|---|
| | | 1.0 | 2.0 | 3.0 |
| 1 | 4.7 | 4.4 | 4.2 | 3.9 |
| 2 | 16.7 | 16.4 | 16.7 | 15.8 |
| 3 | 37.0 | 37.0 | 34.2 | 34.0 |
| Mean | 19.5 | 19.3 | 18.4 | 17.9 |
| Recovery | — | 99% | 94% | 92% |

The results show that there is no clinically significant effect due to even major increases in the albumin level. Note that samples spiked with 3.0 gm/dl represent a very high level of albumin, in the order of 7 gm/dl.

Example 5

Several patient samples were analyzed by the free testosterone procedure using the same tracer as in Example 3 both before and after charcoal absorption. Displayed below are the free testosterone concentrations (in pg/ml) before charcoal absorption, and the percent bound (% $B/B_o$) values following charcoal absorption.

TABLE 24

| Normal Males | | Normal Females | | 3rd Trimester | |
|---|---|---|---|---|---|
| Before | After | Before | After | Before | After |
| 21.24 | 96% | 0.80 | 105% | 4.75 | 99% |
| 14.33 | 98% | 2.32 | 104% | 9.10 | 96% |
| 19.91 | 99% | 1.73 | 104% | 3.58 | 96% |
| 21.03 | 98% | 3.47 | 104% | 4.44 | 97% |
| 15.01 | 95% | 1.93 | 105% | 3.88 | 96% |

The results show, as desired, that charcoal absorption essentially reduces the apparent free testosterone level of patient samples, as measured by the analog procedure, to zero, that is, to percent bound values of approximately TV 100% $B/B_o$. Since charcoal absorption removes testosterone along with other steroids and small molecules from serum sample, while leaving larger molecules such as albumin, SHBG and other binding proteins, this experiment helps to confirm that the analog free testosterone procedure is not influenced by levels of the transport proteins as such.

Example 6

Since non-esterified free fatty acids (NEFA) have a higher association constant to albumin than does testosterone, addition of NEFA should displace free testosterone from albumin. This was confirmed by an experiment in which various amounts of oleic acid were added to each of three patient samples. The effects on the apparent free testosterone levels are shown in Table 24.

TABLE 25

| Oleic Acid Added | Patient 1 | Patient 2 | Patient 3 | Mean |
|---|---|---|---|---|
| 0 mmol/l | 6.2 | 3.3 | 10.0 | 6.5 |
| 2.5 | 7.3 | 4.7 | 11.6 | 7.9 |
| 5.0 | 11.6 | 11.1 | 21.8 | 14.8 |
| 7.5 | 21.2 | 16.0 | 32.3 | 23.2 |
| 10.0 | 30.3 | 17.9 | 47.8 | 32.0 |

Having fully described the invention, it is intended that it be limited solely by the lawful scope of the appended claims.

What is claimed is:

1. A method for determining the concentration of the free testosterone in a biological fluid, wherein said free testosterone is in equilibrium with testosterone bound to one or more endogenous binders in said fluid comprising the steps of (a) forming a mixture of a sample of said fluid with (1) a specific antibody for the free testosterone, and (2) a labeled analog of testosterone which is radioiodinated 6-hydroxy-testosterone-19-carboxymethyl ether histamine that binds to said antibody and has affinity for the endogenous binders lower than that of testosterone for said endogenous binders, (b) maintaining said mixture to permit said labeled analog to compete with the free testosterone for binding with the antibody, (c) measuring the amount of said labeled analog that has, or has not, become bound to the antibody, and (d) determining the concentration of the free testosterone from said measurement, wherein the improvement comprises including in the mixture an amount of a blocking agent which is sulfobromophthalein to inhibit the binding of said labeled analog to the endogenous binders without displacing testosterone bound to said endogenous binders.

* * * * *